United States Patent [19]
Atkin et al.

[11] Patent Number: 5,512,302
[45] Date of Patent: Apr. 30, 1996

[54] PHARMACEUTICAL PROCESS USING STARCH

[75] Inventors: Graham J. Atkin; Peter Drew; John L. Turner, all of Nottinghamshire, United Kingdom

[73] Assignee: The Boots Company PLC, United Kingdom

[21] Appl. No.: 204,191

[22] PCT Filed: Aug. 25, 1992

[86] PCT No.: PCT/EP92/01953

§ 371 Date: Mar. 4, 1994

§ 102(e) Date: Mar. 4, 1994

[87] PCT Pub. No.: WO93/04676

PCT Pub. Date: Mar. 18, 1993

[30] Foreign Application Priority Data

Sep. 6, 1991 [GB] United Kingdom ............... 9119052

[51] Int. Cl.$^6$ ........................................ A61K 9/14
[52] U.S. Cl. ..................... 424/489; 424/488; 424/458; 424/470
[58] Field of Search ..................... 421/489, 488, 421/490, 494

[56] References Cited

U.S. PATENT DOCUMENTS

| | | | |
|---|---|---|---|
| 5,087,454 | 2/1992 | Duerholz et al. | 424/464 |
| 5,240,712 | 8/1993 | Smith et al. | 424/451 |
| 5,260,337 | 11/1993 | Sims et al. | 514/570 |
| 5,266,723 | 11/1993 | Hanna et al. | 562/490 |
| 5,332,834 | 7/1994 | Bhattacharya et al. | 548/339.1 |

FOREIGN PATENT DOCUMENTS

| | | |
|---|---|---|
| 0298666 | 1/1989 | European Pat. Off. . |
| 89/02266 | 3/1989 | WIPO . |
| 9008542 | 8/1990 | WIPO . |

OTHER PUBLICATIONS

Journal of Pharmaceutical Sciences 1989, 78, 68–72, Kawashima et al.

Primary Examiner—Thurman K. Page
Assistant Examiner—William E. Benston, Jr.
Attorney, Agent, or Firm—Ostrolenk, Faber, Gerb & Soffen

[57] ABSTRACT

A process for the preparation of a pharmaceutical composition in the form of agglomerates comprising 70–97% by weight of 2-(4-isobutylphenyl)propionic acid or a pharmaceutically acceptable salt thereof and 3–30% by weight of a starch component, said process comprising the steps of a) forming an emulsion comprising 1) 70–97% by weight of 2-(4-isobutylphenyl)propionic acid or a salt thereof 2) a solvent system 3) 3–30% by weight of the starch component 4) water and optionally 5) a surfactant b) crystallising to produce a suspension comprising crystals of 2-(4-isobutylphenyl)propionic acid or the salt thereof in intimate contact with the starch component c) agitating said suspension to form agglomerates comprising an evenly distributed mixture of 2-(4-isobutylphenyl)propionic acid or a salt thereof and the starch component d) collecting said agglomerates and optionally e) drying said agglomerates. Pharmaceutical formulations comprising 90–99.98% by weight of such a composition together with 0.02–10% of a pharmaceutically acceptable excipient are also described, which are suitable for direct compression into tablets.

28 Claims, No Drawings

PHARMACEUTICAL PROCESS USING STARCH

This invention relates to a process for the preparation of pharmaceutical compositions containing 2-(4-isobutylphenyl) propionic acid or a salt thereof, to compositions produced by said process and to pharmaceutical formulations containing said compositions.

(±)-2-(4-Isobutylphenyl)propionic acid, ibuprofen, is a potent and well tolerated anti-inflammatory, analgesic and anti-pyretic compound. The racemic mixture consists of two enantiomers, namely S(+)-2-(4-isobutylphenyl)propionic acid or S(+)-ibuprofen and R(−)-2-(4-isobutylphenyl)propionic acid or R(−)-ibuprofen. It is known that S(+)-ibuprofen is the active agent and that some R(−)-ibuprofen is converted into S(+)-ibuprofen in humans. The drug has been marketed as the racemic mixture but recent evidence has suggested, however, that in certain circumstances it may be advantageous to administer S(+)-ibuprofen.

The simplest and most cost-effective way to produce a tablet is to dry blend the active ingredient with inexpensive, readily available excipients and to then directly compress the mixture obtained into tablets. For example, aspirin may be dry mixed with starch and the mixture directly compressed into tablets. This method is not suitable for ibuprofen as satisfactory tablets are not produced. Instead the technique of wet granulation is usually employed to produce tablets containing ibuprofen. This means that extra processing steps are required which raise the cost of the tabletting process.

An additional problem is that when ibuprofen is wet granulated by conventional methods, it has been necessary to include a relatively high percentage of excipients to produce satisfactory tablets. As a result, the size of the tablet is increased and consequently high dosage tablets have reduced acceptability to certain patients. There is therefore an acknowledged need for a method of producing smaller ibuprofen tablets containing a high percentage of drug and for an inexpensive, simple process to produce an ibuprofen composition which may be directly compressed into tablets. Various methods have been proposed but an entirely satisfactory solution has yet to be found.

U.S. Pat. No. 4,609,675 discusses the problems of wet granulations containing ibuprofen and discloses a granule comprising 85 to 99% of ibuprofen and 1 to 15% of croscarmellose sodium, a comparatively expensive excipient. The granule is formed by dry mixing the components, passing the resulting mixture through a roller compactor or slugging the composition and thereafter sizing the material obtained.

In the Journal of Pharmaceutical Sciences Vol. 78, p68 (1989), there is disclosed a method of preparing controlled release microspheres of ibuprofen with acrylic polymers by agglomeration in an ethanol/water system. There is no suggestion that this method could be applied to the preparation of conventional release tablets with a controllable microstructure.

EP 298,666 describes a spray dried ibuprofen composition suitable for direct compression into tablets consisting essentially of a spray dried dispersion of ibuprofen in water, pregelatinised starch, a disintegrant and a wetting agent for the ibuprofen. It also discloses tablets prepared from said compositions. This method suffers from several disadvantages. The two principal disadvantages are that the physical properties of the resultant granule cannot be easily adjusted and that the process is very costly both in terms of capital equipment expenditure and running costs due to the high energy input required for the spray drying process.

U.S. Pat. No. 4,911,921 discloses a granular composition comprising 85% or more ibuprofen, a binder, polyvinylpyrrolidone in a film forming amount and moisture up to 2.0%, said granulation being in the form of agglomerates of ibuprofen and binder held together by binder and polyvinylpyrrolidone. The binder is selected from a group consisting of starches, celluloses and sugars. The composition is prepared by fluidising the ibuprofen with a portion of the binder, spraying this blend with a dispersion of the polyvinylpyrrolidone and the remainder of the binder in water and drying the resulting granules. It is disclosed that these granules may be directly compressed into tablets. This process requires extra processing steps involving sophisticated equipment and comparatively high running costs.

Thus none of the above proposed methods offer an entirely satisfactory solution as they involve either a) the incorporation of a comparatively expensive excipient or b) the use of expensive plant equipment in conjunction with high energy consumption. We have now found a cheap, efficient, controllable process for the preparation of a 2-(4-isobutylphenyl)propionic acid composition with an inexpensive excipient. The process may be used with the racemic acid or the S(+)-enantiomer. This composition may be easily modified to give a pharmaceutical formulation which is suitable for direct compression into tablets which have a high content of active ingredient but are of comparatively smaller size than other tablets containing the same amount of active ingredient.

The present invention provides a process for the preparation of a pharmaceutical composition in the form of agglomerates comprising 70–97% by weight of 2-(4isobutylphenyl)propionic acid or a pharmaceutically acceptable salt thereof and 3–30% by weight of a starch component, said process comprising the steps of a) forming an emulsion comprising 1) 70–97% by weight of 2-(4-isobutyl-phenyl)propionic acid or a salt thereof 2) a solvent system 3) 3–30% by weight of the starch component 4) water and optionally 5) a surfactant b) crystallising to produce a suspension comprising crystals of 2-(4-isobutylphenyl)propionic acid or the salt thereof in intimate contact with the starch component c) agitating said suspension to form agglomerates comprising an evenly distributed mixture of 2-(4isobutylphenyl)propionic acid or a salt thereof and the starch component d) collecting said agglomerates and optionally e) drying said agglomerates.

It is very surprising, in view of the elaborate attempts to form a suitable pharmaceutical composition for direct compression containing a high percentage of ibuprofen described previously, that by the comparatively simple process of the present invention it is possible to form homogeneous agglomerates with excellent tabletting properties from an emulsion comprising 2-(4-isobutylphenyl)propionic acid and a starch component. It is surprising that solid agglomerates are formed from the initially deposited particles and that these agglomerates may be easily filtered off in a form in which they have advantageous physical properties for further processing. The process may be carried out as a batch process or a continuous process. It is particularly advantageous that the process may be incorporated as the last step in the synthesis of 2-(4-isobutylphenyl)propionic acid to give the drug in directly compressible form, immediately, without the expense of further processing steps. The considerable economies involved in eliminating extra processing steps and the economies of scale achieved by carrying out the process as part of the chemical synthesis in large reaction vessels mean that this process represents a significant advance in the formulation of this widely used pharmaceutical product.

Another advantage of the present invention is that the process may be performed using 2-(4-isobutylphenyl)propionic acid immediately after it has been collected, for example by filtration, from the last stage of a process to prepare the acid, for example a chemical process, that is without the need for rigorous drying. Thus material which may still be solvent damp, for example after a recrystallisation step using hexane as solvent, may be used directly in the process of the present invention. This represents a significant saving in terms of time and cost.

Yet another advantage of the present invention is that the process gives a very high yield. There is minimal material loss during the process. Taken together all of the advantages result in a very simple, efficient and very cost-effective, reproducible process.

S(+)-Ibuprofen has different physical properties compared to ibuprofen. For example S(+)-ibuprofen melts at 51° C. which is significantly lower than the melting point of ibuprofen which melts at 75°–77° C. Consequently formulation of S(+)-ibuprofen into tablets and intermediate drying and processing steps must be carried out at a lower temperature than would be possible for ibuprofen. Therefore processing times will be increased due to the fact that drying temperatures must be kept low. This difference in melting point also means that certain processing techniques which are used for ibuprofen may be unsuitable for use with S(+)-ibuprofen. In addition, it is difficult to crystallise S(+)-ibuprofen in the for of small crystals, possibly due to the increased solubility of S(+)-ibuprofen in organic solvents. This leads to problems in the preparation of S(+)-ibuprofen tablets which have good strength, dissolution and bioavailability. It is surprising and particularly advantageous that the process of the present invention is also suitable for use with S(+)-ibuprofen to provide valuable compositions with excellent properties capable of providing tablets with good disintegration and bioavailability.

Compressibility, tablet disintegration and dissolution properties are dependent on the size of the agglomerated primary crystals in the compositions, which may be observed by scanning electron microscopy. Specific surface area (in $m^2 \cdot g^{-1}$) is an important indicator of the crystal size and, therefore, of tabletting properties. High surface area compositions (eg 0.5 $m^2 \cdot g^{-1}$) (fine crystal size) deform readily during compaction to form a well-bonded ibuprofen matrix which does not disintegrate and dissolve rapidly. Conversely, low surface area compositions, (eg 0.1 $m^2 \cdot g^{-1}$) with a coarse crystal microstructure, produce mechanically weaker tablets. However, the latter have superior disintegration and dissolution times since a continuous ibuprofen matrix has been avoided. Hence, by controlling the material during processing, a balance is struck between a fine structure with excellent compaction properties and a coarse structure with improved disintegration, dissolution and bioavailability performance. It is a particular advantage of the present invention that the surface area desired for a particular formulation may be obtained by variation of the process conditions, eg the temperature, the relative amounts of starting materials, the cooling rate etc. Suitably the surface area of the agglomerates is in the range 0.05 to 0.8 $m^2 \cdot g^{-1}$, preferably in the range 0.1 to 0.5 $m^2 \cdot g^{-1}$, and most preferably in the range 0.20 to 0.40 $m^2 \cdot g^{-1}$.

The median agglomerate size may be selected as required for the application envisaged. Suitably the median agglomerate size is in the range 50 μm–2 mm, preferably the median agglomerate size is in the range 100 μm–1 mm, more preferably the median agglomerate size is in the range 200–500 μm and most preferably the median agglomerate size is in the range 250–350 μm. The median agglomerate size may be measured by sieve analysis, for example using a vibrating sieve stack.

Suitably the 2-(4-isobutylphenyl)propionic acid, may be the racemic acid (ibuprofen), the substantially pure (+)-enantiomer (S(+)-ibuprofen), the substantially pure (−)-enantiomer (R(−)-ibuprofen) or any mixture of the two enantiomers, for example the eutectic mixture. The term substantially pure is used to indicate that the acid has an enantiomeric purity of at least 90%, that is between 90–100%, preferably greater than 95%, more preferably greater than 99% and most preferably greater than 99.5%, for example greater than 99.9%. Suitably any pharmacologically acceptable salt of ibuprofen or S(+)-ibuprofen may be used. Preferred salts are the sodium salt of S(+)-ibuprofen and the (S)-lysinate salt of S(+)-ibuprofen. Most preferably the 2-(4-isobutylphenyl)propionic acid is ibuprofen or S(+)-ibuprofen.

Preferably the agglomerates comprise 80–94% of 2-(4-isobutylphenyl)propionic acid and 6–20% of a starch component, more preferably 85–93% 2-(4-isobutylphenyl)propionic acid and 7–15% of a starch component and most preferably the agglomerates comprise 87–92% of 2-(4-isobutylphenyl)propionic acid and 8–13% of a starch component. In an especially preferred embodiment, the agglomerates comprise 88–91% of 2-(4-isobutylphenyl)propionic acid and 9–12% of a starch component.

Suitably the starch component may comprise starch or a mixture of two or more starches. Suitable starches include for example potato starch, corn starch, maize starch and wheat starch. The term starch as used herein also encompasses pregelled starches. Pregelled starch is starch that has been chemically and/or mechanically processed to rupture all or part of the granules separated from plants in the presence of water. Suitably the starch component consists of maize starch and/or pregelled maize starch. Preferably the starch component comprises maize starch and pregelled maize starch wherein the weight ratio of maize starch to pregelled maize starch is within the range 25:1 to 1:25. More preferably the ratio of maize starch to pregelled maize starch is within the range 10:1 to 1:10. Most preferably the ratio is 5:1 to 1:1. In an especially preferred embodiment, the ratio of maize starch to pregelled maize starch is 4:1. Preferably the agglomerates comprise from 3–12% by weight of maize starch and from 0.1–6% by weight of pregelled maize starch. More preferably the agglomerates comprise from 6.5–10.5% by weight of maize starch and from 1.5–2.5% by weight of pregelled maize starch.

The solvent system may be a single solvent, or a mixture of one or more solvents, in which 2-(4-isobutylphenyl)propionic acid or a salt thereof is sparingly, partially or completely soluble. Suitably the solvent system may comprise one or more of the following: a ketone (for example acetone or methyl ethyl ketone), an alcohol, preferably a $C_{1-6}$ alkanol (for example methanol, ethanol, propan-1-ol and propan-2-ol), a hydrocarbon (for example hexane, heptane and toluene), a halogenated hydrocarbon (for example dichloromethane), an ester (for example ethyl acetate) or an ether (for example tetrahydrofuran or diethyl ether). Preferably the solvent system comprises a ketone, an alcohol or hydrocarbon. More preferably the solvent system comprises a water-miscible or partially water-miscible solvent, for example ketones (e.g. acetone or methyl ethyl ketone) and $C_{1-6}$ alcohols (e.g. methanol, ethanol, propan-1-ol and propan-2-ol). Most preferably the solvent system comprises acetone or acetone admixed with either hexane or heptane. The ratio of the weight of 2-(4-isobutylphenyl)propionic acid to the weight of the solvent system will depend on the particular solvent system used, the solubility of the acid in this system, and the physical properties, eg surface area, which are required in the agglomerate produced. Similarly the volume of water used in the process may vary. The precise amounts of a particular solvent system and water may be easily determined by those skilled in the art.

Suitably the weight ratio of 2-(4-isobutylphenyl)propionic acid to the solvent system is in the range of 1:0.01 to 1:1000. Preferably the weight ratio of the acid to the solvent system is in the range of 1:0.05 to 1:100. More preferably the weight ratio lies in the range 1:0.1 to 1:10 and most preferably the weight ratio of the acid to solvent system lies in the range of 1:1 to 1:5.

Suitably the weight ratio of the solvent system to water lies in the range of 1:0.1 to 1:1000. Preferably the weight ratio of the solvent system to water lies in the range 1:0.5 to 1:100 and most preferably the weight ratio lies in the range 1:1 to 1:50.

The term surfactant as used herein encompasses emulsifying agents and wetting agents. Any surfactant which is pharmaceutically acceptable may be employed. Suitably the weight ratio of 2-(4-isobutylphenyl)propionic acid to surfactant is in the range of 5000:1 to 100:1. Preferably the weight ratio is in the range 4000:1 to 300:1 and more preferably the weight ratio of 2-(4-isobutylphenyl)propionic acid to surfactant is in the range 3000:1 to 300:1. Preferably the surfactant is sodium lauryl sulphate.

The emulsion may be formed by physical agitation of the solvent system and water. Suitably any method of mixing an organic liquid with water by physical agitation may be used, for example vigorous stirring, shaking and homogenisation. Preferably the emulsion is formed by mixing the solvent system and water with a homogeniser.

Suitably the emulsion is formed at a temperature in the range 1°–100° C. at atmospheric pressure. Preferably the emulsion is formed at a temperature in the range 10°–60° C., more preferably at a temperature in the range 15°–50° C. (for example ambient temperature) and most preferably at a temperature in the range 20°–45° C. In an especially preferred embodiment, the emulsion is formed at 40° C.

Crystallisation may be carried out in a number of ways, for example by cooling the emulsion; by evaporating part of the solvent; by seeding; by adjusting the pH; by mixing with additional liquid in which 2-(4-isobutylphenyl)propionic acid is less soluble, for example, diluting with water; or combinations thereof. Preferably crystallisation is carried out by controlled cooling of the emulsion under homogenisation or by adding the emulsion to cold water with homogenisation.

The agglomerate may be formed by physical agitation of the suspension of the crystals of 2-(4isobutylphenyl)propionic acid or the salt thereof in intimate contact with the starch component, for example by shaking or stirring. The agitation must be enough to maintain intimate contact but not too vigorous otherwise the agglomerate structure will be broken down. It is believed that the agglomerates form as a result of the surface tension of the solvent system binding the particles of the acid and the starch component, which are in intimate contact, together. Initially flocs are produced which increase in size and density to produce agglomerates. It will be understood that the agglomerates are solid. It will also be understood by those skilled in the art that the crystallisation and agglomerate formation may, depending on the reaction conditions, occur so rapidly that they appear to be occurring simultaneously.

The agglomerates may be collected by filtration or by centrifugation or other methods, known to those skilled in the art, of separating solids from a supernatant liquid. Preferably the agglomerates are collected by filtration or by centrifugation. More preferably the agglomerates are collected by filtration.

The agglomerates may be dried by methods known to those skilled in the art. Suitably the agglomerates are dried at atmospheric pressure or under reduced pressure. Optionally the agglomerates may be agitated or rotated during the drying process and optionally the agglomerates may be dried above ambient temperature for example at a temperature in the range of 20°–60° C. When the agglomerates comprise S(+)-ibuprofen preferably the agglomerates are dried at a temperature in the range of 20°–40° C.

The homogeneous nature of the agglomerates of the present invention may be observed by electron microscopy. In addition, the homogeneity of the granules is confirmed by analysing the 2-(4-isobutylphenyl)propionic acid content of samples of the agglomerates by high performance liquid chromatography (HPLC).

The moisture content of the granules, after drying, may be measured by recording the weight loss from an equilibrated sample of the agglomerate after storage over phosphorus pentoxide under vacuum at ambient temperature. Suitably the moisture content of the agglomerates is in the range of 0.1 to 3.0% by weight. Preferably the moisture content of the agglomerates is in the range of 0.5 to 1.5% by weight.

The emulsion comprising a salt of 2-(4-isobutylphenyl)propionic acid may be formed by neutralising the acid with a base to form the salt in situ.

In a more preferred form, the process of the present invention comprises a) dissolving 2-(4-isobutylphenyl)propionic acid in a solvent system to form a solution b) mixing the solution with a dispersion of a starch component in water containing a surfactant to form an emulsion c) crystallising to produce a suspension comprising crystals of 2-(4-isobutylphenyl)propionic acid in intimate contact with the starch component d) agitating said suspension to form agglomerates comprising and evenly distributed mixture of the acid and the starch component e) collecting said agglomerates and optionally f) drying said agglomerates.

In a most preferred process, the present invention provides a process for the preparation of a pharmaceutical composition in the form of agglomerates comprising 70–97% of S(+)-2-(4-isobutylphenyl)propionic acid and 3–30% of a starch component comprising:

a) forming an emulsion comprising
1) 1 part by weight of 2-(4isobutylphenyl)propionic acid
2) 0.1–0.2 parts by weight of a solvent system
3) 0.05–0.25 parts by weight of maize starch
4) 0.01–0.06 parts by weight of pregelled maize starch
5) 0.5–3.0 parts by weight of water
6) 0.0001–0.005 parts by weight of sodium lauryl sulphate at a temperature in the range of 15°–50° C.

b) mixing this emulsion with 1–10 parts by weight of water at a temperature in the range of 0°–20° C. to form a suspension which agglomerates c) collecting said agglomerates by filtration and d) drying said agglomerates.

The pharmaceutical compositions prepared by the above processes are novel intermediates useful in the preparation of pharmaceutical formulations. These pharmaceutical compositions form another aspect of the present invention.

Thus the present invention provides a pharmaceutical composition in the form of agglomerates comprising 70–97% by weight of 2-(4-isobutylphenyl)propionic acid and 3–30% by weight of a starch component. Preferably the agglomerates comprise 80–94% by weight of the acid and 6–20% by weight of a starch component, more preferably 85–93% by weight of the acid and 7–15% by weight of the starch component and most preferably the agglomerates comprise 87–92% by weight of 2-(4-isobutylphenyl)propionic acid and 8–13% by weight of a starch component. In an especially preferred embodiment of the present invention, the agglomerate comprises 88–91% by weight of 2-(4-isobutylphenyl)propionic acid and 9–12% by weight of a starch component. Preferably the 2-(4-isobutylphenyl)propionic acid comprises the racemic form or the S(+)-enantiomer in substantially pure form.

The agglomerates of the present invention containing 2-(4-isobutylphenyl)propionic acid or a salt thereof and starch are suitable for incorporation into pharmaceutical formulations. These formulations form another aspect of the present invention. Accordingly the present invention provides a pharmaceutical formulation comprising 70–99.98% by weight, more preferably 80–95% and most preferably 86–92% by weight of a composition of the present invention together with one or more pharmaceutically acceptable excipients.

The pharmaceutically acceptable excipient may be combined with the agglomerates by methods known to those skilled in the art, for example by basing and blending. In a preferred form of the present invention, the pharmaceutically acceptable excipient may be incorporated with the agglomerates during the drying of the agglomerates thus achieving process economies by avoiding the use of separate operations.

The agglomerates may be dried for example in a vacuum rotary drier wherein the agglomerates are placed in a vessel equipped with agitator blades which stir the agglomerates optionally under vacuum and optionally with heating. After removal of water and solvents from the agglomerates, one or more pharmaceutically acceptable excipients may be added and the mixture blended by the agitator blades for a suitable time to produce a homogeneous pharmaceutical formulation which may optionally be sieved to the required mesh size before the material is directly compressed into tablets. Alternatively, a rotating cylindrical drier without agitator blades or other types of drier known to those skilled in the art may be used.

Suitable pharmaceutically acceptable excipients for use in such formulations are well known in the art of pharmacy. Preferably the pharmaceutically acceptable excipient comprises one or more diluents (for example lactose, calcium phosphate, dextrin, microcrystalline cellulose, sucrose, starch, calcium sulphate or mixtures thereof); and/or one or more lubricating agents (for example magnesium stearate, stearic acid, calcium stearate or mixtures thereof); and/or one or more flow aids (for example talc or silicon dioxide) and/or one or more binders (for example microcrystalline cellulose) and/or one or more disintegrants (for example microcrystalline cellulose, maize starch, sodium starch glycolate, low substituted hydroxypropyl cellulose, alginic acid or croscarmellose sodium or mixtures thereof). A more preferred formulation comprises 90–99.98% by weight of a composition of the present invention, 0.01–5% of a lubricating agent and 0.01–5% of a flow aid. Suitably any pharmaceutically acceptable lubricating agent or flow aid may be used. Preferably the lubricating agent is magnesium stearate. Preferably the flow aid is colloidal silicon dioxide.

In a most preferred process, one or more lubricating agents and/or one or more flow aids are thoroughly mixed with the agglomerates during the drying process to produce a pharmaceutical formulation which is suitable for direct compression into tablets.

In therapeutic use, the formulations of the present invention may be administered orally, rectally, parenterally or topically. Thus the therapeutic formulations of the present invention may be presented in any of the known pharmaceutical forms for oral, rectal, parenteral or topical administration. The formulations of the invention are generally prepared in unit dosage form. Preferably the unit dosage of active ingredient is 50–1000 mg for example 100 mg, 200 mg, 400 mg, 600 mg or 800 mg. The excipients used in the preparation of these compositions are the excipients known in the pharmacist's art.

Formulations for oral administration are preferred formulations of the invention and there are known pharmaceutical forms for such administration, for example tablets and capsules. Tablets are a preferred form due to the fact that it is an important advantage of the formulations of the present invention that they can be directly compressed into tablets containing a high dose of ibuprofen but with reduced overall dimensions compared to other tablets containing a similar dose of ibuprofen. Tablets may be prepared by mixing the agglomerates of the present invention with one or more lubricating agents (for example magnesium stearate) and one or more flow aids (for example colloidal silicon dioxide) and forming the mixture into tablets by known methods. The incorporation of the lubricating agent and/or the flow aid is preferably carried out during the drying of the agglomerates but may be carried out as a separate process step.

Such tablets may, if desired, be provided with enteric coatings by known methods, for example by use of cellulose acetate phthalate. Similarly, capsules, for example hard or soft gelatin capsules, containing agglomerates of the present invention with or without added excipients, may be prepared by conventional means and, if desired, provided with enteric coatings in a known manner. The tablets and capsules may conveniently each contain from 50 to 1000 mg of the ibuprofen/starch agglomerates. Preferably the tablets comprise 50 mg, 100 mg, 200 mg, 400 mg, 600 mg, 800 mg or 1000 mg of 2-(4-isobutylphenyl)propionic acid. The tablets may be formulated in a manner known to those skilled in the art so as to give a controlled release of 2-(4-isobutylphenyl)propionic acid or a salt thereof.

Problems can be experienced with conventional ibuprofen formulations containing starch due to cracking of the film-coat or the sugar-coat. It is believed that this occurs as a result of expansion of the tablet core caused by absorption of water by the starch. Advantageously this problem is minimised in formulations of the present invention since the amount of starch is lower than the amount used in conventional formulations.

The compositions and formulations of the present invention may, if desired, be combined with other compatible pharmacologically active ingredients (for example centrally acting analgesics, eg codeine) and/or enhancing agents. Thus, for example, the compositions may be combined with any ingredient commonly used in a cough or cold remedy, for example caffeine or another xanthine derivative, and/or another analgesic, and/or a skeletal muscle relaxant, and/or an antihistamine, and/or a decongestant, and/or a cough suppressant and/or an expectorant.

Suitable antihistamines which are preferably non-sedating include acrivastine, astemizole, azatadine, azelastine, bromodiphenhydramine, brompheniramine, carbinoxamine, cetirizine, chlorpheniramine, cyproheptadine, dexbrompheniramine, dexchlorpheniramine, diphenhydramine, ebastine, ketotifen, lodoxamide, loratidine, levocubastine, mequitazine, oxatomide, phenindamine, phenyltoloxamine, pyrilamine, setastine, tazifylline, temelastine, terfenadine, tripelennamine or triprolidine. Suitable cough suppressants include caramiphen, codeine or dextromethorphan. Suitable decongestants include pseudoephedrine, phenylpropanolamine and phenylephrine. Suitable expectorants include guafensin, potassium citrate, potassium quaiacolsulphonate, potassium sulphate and terpin hydrate.

2-(4-Isobutylphenyl)propionic acid is an anti-inflammatory, analgesic and anti-pyretic agent. The formulations of the present invention are therefore, indicated for use in the treatment of rheumatoid arthritis, osteoarthritis, ankylosing spondylitis, seronegative arthropathies, periarticular disorders and soft tissue injuries. They may also be used in the treatment of postoperative pain, postpartum pain, dental pain, dysmenorrhoea, headache, musculoskeletal pain or the pain or discomfort associated with the following: respiratory infections, colds or influenza, gout or morning stiffness.

The invention is illustrated by the following non-limitative Examples. The ibuprofen used was that supplied commercially by the Boots Company PLC. S(+)-Ibuprofen was prepared by resolving ibuprofen with (−)-methylbenzylamine in a similar manner to that described in J. Pharm. Sci. 65 (1976) 269–273.

Typically the compositions of the agglomerates produced were examined by electron microscopy. The surface areas were measured using a Micromeritics Gemini instrument using a five point analysis at partial pressures of 0.1, 0.15, 0.2, 0.25 and 0.3 using nitrogen gas. This instrument was calibrated using stable aluminium oxide powders which had been certified using a Micromeritics ASAP 2000 instrument.

EXAMPLE 1

Ibuprofen (200.0 g) was dissolved in acetone (200 ml) at 40° C. This solution was added with agitation to a mixture of maize starch (30.0 g), sodium lauryl sulphate (240 mg) and water (1200 ml) at 40° C. in a 10 liter vessel fitted with a water cooling jacket. The resulting mixture was emulsified using a Silverson high-speed multi-purpose emulsifier operating at the minimum speed required to maintain a good emulsion. The mixture was cooled at a rate of 0.5°–3.0° C./min until agglomerates formed. At this point, the emulsifier was switched off and cooling continued under gentle stirring. The agglomerates were collected by vacuum filtration and dried at 40°–50° C. under atmospheric pressure. Surface area 0.56 m$^2$. g$^{-1}$.

EXAMPLES 2–6

The following examples were prepared using the procedure described in Example 1 but replacing the maize starch with a mixture of maize starch and pregelled maize starch as shown in Table 1.

TABLE 1

| EXAMPLE | MAIZE STARCH (g) | PREGELLED MAIZE STARCH (g) |
| --- | --- | --- |
| 2 | 0 | 20 |
| 3 | 10 | 10 |
| 4 | 14 | 6 |
| 5 | 16 | 4 |
| 6 | 18 | 2 |

EXAMPLE 7

Ibuprofen (200 g) was dissolved in a warm (>40° C.) mixture of acetone (166 ml) and hexane (7.2 ml). This solution was added to a warm mixture of maize starch (16.0 g), pregelled maize starch (4.0), sodium lauryl sulphate (67 mg) and water (334 ml) as described in Example 1. The surface area of the product obtained was 0.40 m$^2$. g$^{-1}$.

EXAMPLES 8–10

The procedure described in Example 7 was followed but the amount of hexane was varied as shown in Table 2.

TABLE 2

| Example | % w/w of hexane based on ibuprofen | Product Surface Area (m$^2 \cdot$ g$^{-1}$) |
| --- | --- | --- |
| 8 | 10 | 0.21 |
| 9 | 5 | 0.29 |
| 10 | 2.5 | 0.18 |

EXAMPLE 11

A solution of ibuprofen (9 kg) in acetone (7.5 l) and hexane (325 ml) was warmed to 40° C. and then added to a mixture of maize starch (720 g), pregelled starch (180 g), sodium lauryl sulphate (3 g) and water (15 l) at 40° C. in a 50 liter Giusti Cosmix cream production vessel equipped with a water cooling facility. The mixture was emulsified using a homogenising head set into the base of the vessel and simultaneously slowly stirred at approximately 30 revolutions per minute using a gate stirrer with wall scrapers. The temperature of the emulsion was lowered by controlled cooling (0.3° C. per minute) until a precipitation exotherm occurred. The solution was maintained at this temperature until agglomerates formed. The homogeniser head was switched off and cooling continued until the temperature reached 20° C. The product was collected by vacuum filtration and then dried at 40°–50° C. Surface Area—0.28 m$^2$. g$^{-1}$.

EXAMPLES 12–18

Examples 12 to 18 were prepared in a similar manner to Example 11. The products were examined for particle size distribution (sieve analysis), surface area and appearance (electron microscopy, SEM ISI SS60). The results obtained are shown in Table 3.

The samples were combined together in order to produce blends with similar median sizes and surface area. Examples 12, 13 and 18 were combined to give batch A and Examples 15, 16 and 17 were combined to give batch B. These batches were produced by combining the products from the three examples using a blender (KEK, 50 kg drum size) for 20 minutes at 24 rpm.

TABLE 3

| Example | Sieve Analysis (μm) | | | Surface Area $(m^2 \cdot g^{-1})$ |
|---|---|---|---|---|
| | Lower | Median | Upper | |
| 12 | 56 | 112 | 592 | 0.299 |
| 13 | 73 | 243 | 743 | 0.373 |
| 14 | 63 | 129 | 623 | 0.378 |
| 15 | 67 | 154 | 666 | 0.348 |
| 16 | 55 | 109 | 522 | 0.353 |
| 17 | 116 | 158 | 420 | 0.357 |
| 18 | 61 | 123 | 605 | 0.381 |
| Batch A 12 + 13 + 18 | 56 | 112 | 532 | 0.351 |
| Batch B 15 + 16 + 17 | 52 | 104 | 433 | 0.361 |

| | Density (g/cc) | |
|---|---|---|
| | Bulk | Tap |
| Batch A | 0.42 | 0.54 |
| Batch B | 0.44 | 0.56 |

Agglomerates formed in the Examples were analysed for ibuprofen content by HPLC. Specimen results obtained are shown in Table 4.

TABLE 4

| | EXAMPLE 11 | BATCH A |
|---|---|---|
| Ibuprofen Content | 89.6 | 88.4 |
| Water (Karl Fischer) | 0.4 | 0.9 |
| Acetone (Headspace) | <0.1 | <0.1 |
| Hexane (Headspace) | <0.1 | <0.1 |
| Degradation Products (HPLC) | <0.1 | <0.1 |

EXAMPLE 19

In a similar manner to Example 1, S(+)-ibuprofen (60 g) was dissolved in warm acetone (50 ml) at 35° C. This solution was added to a mixture of maize starch (4.8 g), pregelled maize starch (1.2 g), sodium lauryl sulphate (70 mg) and water (350 ml) at 35° C. with homogenisation. The mixture was cooled in a controlled manner and the agglomerates collected by filtration and dried. Surface Area—0.36 $m^2 \cdot g^{-1}$.

EXAMPLE 20

In a similar manner to Example 19 using the same quantities of reactants, the acetone solution of S(+)-ibuprofen was prepared at ambient temperature and added to the starch mixture at ambient temperature. The mixture was stirred at this temperature until agglomerates were formed and these were collected by filtration and dried. Surface Area—0.58 $m^2 \cdot g^{-1}$.

Examples 21–29 were prepared as summarized in Table 5 and the following notes.

EXAMPLE 21

This was prepared in a similar manner to Example 19 but varying the temperature of the organic phase and the aqueous phase.

EXAMPLE 22

The organic phase was prepared as described in Table 5 and then crash cooled by pouring into the aqueous phase at 12° C. under homogenisation. Rapid precipitation into agglomerates occurred. The clarity of the resultant liquid phase indicated that the majority of the starch had been incorporated into these particles and this was confirmed by examination of micrographs.

TABLE 5

| Example | Organic Phase | | | Aqueous Phase | | | | | Additional | |
|---|---|---|---|---|---|---|---|---|---|---|
| | S (+) (Kg) | Acetone (ml) | Temp (°C.) | Water (ml) | Maize Starch (g) | Pregelled Starch (g) | SLS (g) | Temp (°C.) | Water (ml) | Temp (°C.) |
| 21 | 1.0 | 200 | 40 | 2000 | 80 | 20 | 0.4 | 30 | — | — |
| 22 | 1.0 | 200 | 40 | 2000 | 80 | 20 | 0.4 | 12 | — | — |
| 23 | 1.0 | 200 | 40 | 400 | 80 | 20 | 0.4 | 40 | 1600 | 15 |
| 24 | 1.0 | 200 | 40 | 400 | 80 | 20 | 1.0 | 40 | 1600 | 12 |
| 25 | 1.0 | 200 | 40 | 400 | 80 | 20 | 1.0 | 40 | 1600 | 12 |
| 26 | 1.0 | 200 | 40 | 400 | 80 | 20 | 1.0 | 40 | 7000 | 15 |
| 27 | 0.7 | 140 | 40 | 400 | 80 | 20 | 1.0 | 40 | 1600 | 15 |
| 28 | 0.7 | 140 | 40 | 400 | 80 | 20 | 1.8 | 40 | 1600 | 12 |
| 29 | 0.4 | 80 | 40 | 400 | 80 | 20 | 1.0 | 40 | 1600 | 12 |

S(+) represents S(+)-ibuprofen
SLS represents sodium lauryl sulphate
Temp represents temperature

EXAMPLES 23–29

In each example, the organic phase was combined with the aqueous phase with reduced water content at 40° C. The composition of each phase is given in Table 5. This mixture was homogenised to give a stable emulsion. Additional water (volume and temperature as in Table 5) was added to the emulsion and agglomerates were formed which were collected by filtration and dried.

Surface area measurements were measured using a Micromeritics Gemini instrument with nitrogen as the adsorbate gas and electron micrographs (ISI SS60 SEM) were recorded for the products from Examples 22, 23 and 24. The results are shown in Table 6.

TABLE 6

| EXAMPLE | 22 | 23 | 24 |
|---|---|---|---|
| Surface Area (m² · g⁻¹) | 0.42 | 0.43 | 0.54 |

Tablet Production - Racemic Ibuprofen

Five kilogrammes of the agglomerates from Example 11 were based and blended with magnesium stearate (0.8% by weight) and colloidal silicon dioxide (0.1% by weight). This material was compressed on a Manesty Betapress machine fitted with 12.7 mm deep curvature tooling. Compacts weighing 666 mg were compressed giving an ibuprofen dosage of 600 mg per tablet (90% ibuprofen). The machine was set to produce a tablet of crushing strength equal to 7 Kgf using a low level of precompression. No problems with flow, lamination or sticking were encountered. The tablets produced were sealed in containers for 24 hours prior to testing for both crushing strength and disintegration time (British Pharmacopoeia (BP) 1973 method). Table 7 summarises the measured properties.

TABLE 7

RESULTS OF THE COMPRESSING TRIAL

| Measurement | Mean | Standard Deviation |
|---|---|---|
| Weight (mg) | 667.60 | 11.41 |
| Thickness (mm) | 7.34 | 0.04 |
| Diameter (mm) | 12.69 | 0.01 |
| Crushing Strength (Kgf) | 7.81 | 1.78 |
| BP 1973 Disint.Time (s) | 64 | 10 |

Stability Testing

Tablets prepared above from the ibuprofen starch agglomerates of Example 11 were coated with 35 mg of a hydroxypropylmethylcellulose based film coat and compared to film coated ibuprofen 600 mg tablets prepared from granules produced by a normal high shear wet granulation process. A long term stability study was set up between these tablets and a normal production batch of coated ibuprofen 600 mg tablets. In all cases, samples were stored in high density polythene containers with waxed aluminium cap liners. The results of the stability testing are listed in Table 8. The dissolution experiments were carried out using the US Pharmacopeia XXII, Apparatus II method. T50 and T90 values are the times for 50% and 90% , respectively, of a standard concentration of drug to be detected spectrographically during dissolution testing. Initial ibuprofen starch agglomerate tablet dissolution times are higher than those normally associated with ibuprofen tablets. Results taken over a 12 month time period indicate that tablets prepared from the ibuprofen starch agglomerates maintain approximately constant dissolution values under all the stability testing conditions used.

Tablet Production 2

Magnesium stearate (0.8% by weight) and colloidal silicon dioxide (0.1% by weight) were sieved (500 μm) and added to batches A and B (see earlier), respectively. The resultant mixtures were blended for 20 minutes (KEK, 50 kg drum size) for 20 minutes at 24 rpm. Batch A (blended) and batch B (blended) were compressed using a compaction simulator.

Tablet Production 3 (S(+)-Ibuprofen)

The products from Examples 22, 23 and 24 were sieved through a 1400 μm mesh and blended with colloidal silicon dioxide (0.1% by weight) and magnesium stearate (0.8% by weight). This material was compressed on a Compaction Simulator fitted with 11 mm deep curvature tablets to a target weight of 444 mg (400 mg of S(+)-ibuprofen per tablet).

The tablets obtained had crushing strengths in excess of 4 Kgf and disintegration times of less than 2 minutes.

TABLE 8

DISSOLUTION RESULTS USP (II) 50 RPM

| Time | (Storage Temperatures) | | | | | |
|---|---|---|---|---|---|---|
|  | Ambient | | 30° C. | | 40° C. | |
| (months) | T50 (mins) | T90 (mins) | T50 (mins) | T90 (mins) | T50 (mins) | T90 (mins) |
| a) Tablets prepared from ibuprofen starch agglomerates | | | | | | |
| 0 | 14.9 | 25.7 | | | | |
| 3 | 13.3 | 25 | 10.9 | 21.9 | 10.3 | 20.9 |
| 6 | 15.7 | 26.2 | 8.1 | 17 | 11.4 | 20.9 |
| 12 | 10.9 | 20.8 | 7.3 | 17 | 10.3 | 28.6 |
| b) Comparative study 600 mg ibuprofen tablets | | | | | | |
| 0 | 5.6 | 10.9 | | | | |
| 3 | 6.1 | 15.1 | 6.6 | 16.7 | 7.8 | 20.5 |
| 6 | 5.9 | 13.4 | 6.0 | 14.8 | 8.4 | 20.4 |
| 12 | 5.6 | 11.9 | 6.7 | 14.3 | 20.9 | 32.0 |

We claim:

1. A process for the preparation of a solid pharmaceutical composition in the form of agglomerates having a particle size in the range 50 to 2000 μm and a surface area in the range 0.05–0.8 m²g⁻¹ and comprising 70–97% by weight of 2-(4isobutylphenyl)propioni acid or a pharmaceutically acceptable salt thereof and 3–30% by weight of a starch, said process comprising the steps of a) forming an emulsion comprising 1) 70–97% by weight of 2-(4-isobutylphenyl)propionic acid or a salt thereof 2) a solvent system 3) 3–30% by weight of the starch 4) water and optionally 5) a surfactant b) crystallizing to produce a suspension comprising crystals of 2(4-isobutylphenyl)propionic acid or the salt thereof in intimate contact with the starch c) agitating said suspension to form agglomerates comprising an evenly distributed mixture of 2(4-isobutylphenyl)propionic acid or a salt thereof and the starch d) collecting said agglomerates and optionally e) drying said agglomerates.

2. A process according to claim 1 wherein the agglomerates comprise 87–92% by weight of 2-(4-isobutylphenyl)propionic acid and 8–13% by weight of a starch.

3. A process according to either claim 1 wherein the surface area of the agglomerates is in the range 0.1 to 0.5 $m^2 g^{-1}$.

4. A process according to claim 1 wherein the median particle size of the agglomerates is in the range 200–500 μm.

5. A process according to claim 1 wherein the weight ratio of 2-(4-isobutylphenyl)propionic acid to the solvent system is in the range of 1:1 to 1:50.

6. A process according to claim 1 wherein the solvent system comprises one or more of the following: a hydrocarbon, a ketone or an alcohol.

7. A process according to claim 1 wherein the solvent system comprises one or more of the following: a water-miscible or partially water-miscible ketone, a $C_{1-6}$ alcohol, hexane or heptane.

8. A process according to claim 1 wherein the starch comprises maize starch and pregelled maize starch wherein the weight ratio of maize starch to pregelled maize starch is within the range 25:1 to 1:25.

9. A process according to claim 1 wherein the weight ratio of the solvent system to water lies in the range of 1:0.1 to 1:1000.

10. A process according to claim 1 wherein the surfactant is present and the weight ratio of 2-(4isobutylphenyl)propionic acid to the surfactant is in the range of 5000:1 to 100:1.

11. A process according to claim 1 wherein the 2-(4-isobutylphenyl)propionic acid is crystallised by cooling the emulsion or diluting with water.

12. A process according to claim 1 wherein the agglomerates are collected by filtration.

13. A process according to claim 1 wherein the 2-(4-isobutylphenyl)propionic acid is in the racemic form.

14. A process according to claim 1 wherein the acid is substantially pure S(+)-2-(4isobutylphenyl)propionic acid.

15. A pharmaceutical composition prepared according to claim 1.

16. A solid pharmaceutical composition in the form of agglomerates having a particle size in the range 50 to 2000 μm and a surface area in the range 0.05–0.8 $m^2 g^{-1}$ and consisting essentially of 70–97% by weight of 2-(4isobutylphenyl)propionic acid and 3–30% by weight of a starch.

17. A pharmaceutical composition according to or claim 16 consisting essentially of 87–92% by weight of 2-(4-isobutylphenyl)propionic acid and 8–13% by weight of a starch.

18. A pharmaceutical composition according to claim 17 wherein the starch comprises from 6.5–10.5% by weight of maize starch and from 1.5–2.5% by weight of pregelled maize starch.

19. A composition according to any one of claim 16 wherein the 2-(4-isobutylphenyl)propionic acid is in the racemic form.

20. A composition according to claim 16 wherein the acid is substantially pure S (+) -2- (4isobutylphenyl)propionic acid.

21. A pharmaceutical formulation comprising 70–99.98% by weight of a composition according to claim 16 together with a pharmaceutically acceptable excipient.

22. A pharmaceutical formulation according to claim 21 wherein the pharmaceutically acceptable excipient comprises one or more diluents, one or more lubricating agents or one or more flow aids or one or more binders, or one or more disintegrants or mixtures thereof.

23. A pharmaceutical formulation according to claim 22 wherein the pharmaceutical formulation comprises 90–99.98% by weight of a said composition claim 15 0.01–5% of a lubricating agent and 0.01–5% of a flow aid.

24. A process to prepare a pharmaceutical formulation wherein a pharmaceutical composition according to claim 16 is blended with a pharmaceutically acceptable excipient.

25. A process to prepare a pharmaceutical formulation according to claim 15 wherein the pharmaceutically acceptable excipient is blended with the pharmaceutical composition during the drying of the pharmaceutical composition.

26. A pharmaceutical composition prepared according to claim 2.

27. A pharmaceutical composition prepared according to claim 3.

28. A pharmaceutical composition prepared according to claim 8.

* * * * *